United States Patent
Viscomi et al.

(10) Patent No.: US 6,913,573 B1
(45) Date of Patent: Jul. 5, 2005

(54) POSITIVE-PRESSURE RECTAL INCONTINENCE PAD

(76) Inventors: Dominic Anthony Viscomi, 1868 Felicity La., Hellertown, PA (US) 18055; Brian David Viscomi, 500 Central Ave., Union City, NJ (US) 78087

(*) Notice: Subject to any disclaimer, the term of this patent is extended or adjusted under 35 U.S.C. 154(b) by 163 days.

(21) Appl. No.: 10/420,048

(22) Filed: Apr. 21, 2003

(51) Int. Cl.$^7$ .................. A61F 2/00; A61F 13/20; A61F 5/44

(52) U.S. Cl. ............... 600/29; 604/328; 604/355; 604/385.01

(58) Field of Search ................. 604/304–307, 604/327, 328, 355, 358, 377, 385.01, 385.31, 386, 387, 277–279, 330, 337, 354, 285.17, 285.18, 904; 600/29–32

(56) References Cited

U.S. PATENT DOCUMENTS

| | | | |
|---|---|---|---|
| 1,561,020 A | * 11/1925 | Pond | 604/287 |
| RE24,385 E | * 10/1957 | Flanders | 604/364 |
| 3,512,527 A | * 5/1970 | Desoye et al. | 604/57 |
| 3,559,650 A | * 2/1971 | Larson | 604/364 |
| 3,570,489 A | * 3/1971 | Brown | 604/328 |
| 3,881,485 A | * 5/1975 | Davis, Jr. | 604/286 |
| 3,958,556 A | * 5/1976 | Schenk | 600/32 |
| 4,182,335 A | * 1/1980 | Matrullo | 604/365 |
| 4,209,009 A | * 6/1980 | Hennig | 600/30 |
| 4,445,899 A | * 5/1984 | Bond | 604/385.01 |
| 4,484,919 A | 11/1984 | Sohn et al. | |
| 4,880,417 A | * 11/1989 | Yabrov et al. | 604/355 |
| 4,979,947 A | * 12/1990 | Berman | 604/369 |
| 4,981,465 A | * 1/1991 | Ballan et al. | 600/32 |
| 5,074,855 A | * 12/1991 | Rosenbluth et al. | 604/385.17 |
| D325,969 S | * 5/1992 | Davy | D24/124 |
| 5,520,675 A | * 5/1996 | Knox-Sigh | 604/385.17 |
| 5,624,307 A | * 4/1997 | Lenear et al. | 452/176 |
| 5,665,081 A | * 9/1997 | Grosse | 604/359 |
| 5,695,484 A | 12/1997 | Cox | |
| 5,924,423 A | * 7/1999 | Majlessi | 128/897 |
| 6,013,023 A | * 1/2000 | Klingenstein | 600/29 |
| RE36,994 E | * 12/2000 | Anderberg | 452/176 |
| 6,221,004 B1 | * 4/2001 | Kahl | 600/29 |
| 6,313,371 B1 | * 11/2001 | Conant et al. | 604/359 |
| 6,428,467 B1 | * 8/2002 | Benderev | 600/30 |
| 6,461,341 B1 | 10/2002 | Bennett | |
| 2001/0003157 A1 | * 6/2001 | Toth | 606/197 |
| 2004/0068245 A1 | * 4/2004 | Rana et al. | 604/385.17 |
| 2004/0162537 A1 | * 8/2004 | Manasek | 604/385.01 |

FOREIGN PATENT DOCUMENTS

| DE | 37 40 208 A 1 | * 6/1989 | A61F/13/20 |
|---|---|---|---|
| EP | 0 350 871 A2 | * 1/1990 | A61F/13/00 |

OTHER PUBLICATIONS http://www.nationalgeographic.com/earthpulse/reef/reef2.html, Virtual World, Great Barrier Reef, 1996–2004, National Geographic Society, Image Gallery, Nudibranch, p. 1.*

* cited by examiner

Primary Examiner—Larry I. Schwartz
Assistant Examiner—Michael G. Bogart (57) ABSTRACT

An ergonomically contoured, snail shaped rectal pad comprising a highly compressible pressure-producing node (2) contiguous to a thin blade-like structure called a tail (4) enveloped in an absorbent sheath. Surrounding these structures are two flap-like lateral wings (6), which form the posterior groove (12). Emerging from the posterior groove is the insertion aperture (10) and the removal tab (14). Encasing the pad is a highly absorbent sheath (16).

17 Claims, 8 Drawing Sheets

POSITIVE-PRESSURE RECTAL INCONTINENCE PAD

CROSS-REFERENCE TO RELATED APPLICATION

Not applicable

FEDERALLY SPONSORED RESEARCH

Not Applicable

SEQUENCE LISTING OR PROGRAM

Not Applicable

BACKGROUND OF THE INVENTION

1. Field of Invention

This invention relates to the field of medical devices, specifically to a positive pressure producing rectal collection pad aimed at coping with and countering the effects of bowel incontinence.

2. Background of the Invention

Fecal incontinence is an uncomfortable, inconvenient and embarrassing condition, which is experienced by upwards of twenty percent of the world's population. It can result from many afflictions including: irritable bowel syndrome, colitis, post-colorectal cancer surgery and or pelvic radiation treatments, transient illnesses and a broad array of prescription medications. Prior attempts to alleviate the symptoms of this problem have been to some degree inadequate. Bowel compromised individuals experience periodic episodes of intestinal peristaltic waves of urgency from food intake and or nervous stimuli, resulting in accidental soiling and or immediate need to go to toilet. Irritable bowel produces a concomitant mixture of intestinal gas and downward movement of fecal material through the intestinal tract.

The anal sphincter can also overestimate this fecal accumulation such that it wants to release rather than wait for adequate residue to produce a normal bowel movement. Furthermore, the sphincter has a diminished capacity to distinguish between gaseous and solid buildup, contributing further to incontinence. A normal functioning sphincter can permit gaseous discharge while blocking solid material discharge. Current treatments for bowel incontinence include bulky diapers and undergarments, dietary control, medications, psychological counseling, and other proposed perineal specific dressings. Specifically concerning the latter, functional rectal incontinence pads have been proposed to address acute symptoms. People suffering from fecal incontinence generally experience a diminished quality of life as a result of this affliction and prior art's inadequate solution to addressing this problem.

Prior arts' rectal pads have attempted to solve the problem of fecal incontinence by serving as collection devices of varied shapes and sizes which simply rest in the gluteal cleft, and serve as a barrier and a receptacle for involuntary discharge of anal contents. Though attempting to address the problem of discharge collection, these rectal pads still have significant shortcomings inherent to their design and construction. The void existing between the pads' superior surface and anal opening can allow for an undesirable residue to persist in spite of the pad's presence. Therefore, a solution is needed to supersede the prior arts' inadequate designs and sole ability to passively collect the effects of an accidental release of fecal material. The remedy to prior arts' shortcomings comprises a pad of vastly improved ergonomic design. One which has a pressure inducing non-invasive nodule feature that actively helps a sufferer of fecal incontinence to stave off bowel urges with greater success and comfort, and ultimately gain greater ability to control bowel urges through the unique dynamic features of this device.

The rectal pad in U.S. Pat. No. 4,084,919 to Sohn et al. lacks significant ergonomics insofar that the device is a straight, rather substantial and inflexible wedge, that does not promote truly intimate contact with the anal region. Though it serves as a wide barrier to collect any accidental discharge, the issue of comfort is questionable with the wearer sitting down or engaging in vigorous activity. Furthermore, the adhesive fasteners comprises two opposed rather elongated strips which complicate implementation of the device, and also demands greater time applying and changing during frequent bouts of accidental discharge. This is particularly unfavorable in public or workplace environments where time and location may factor heavily. Also questionable, due to the adhesive means of fastening, is the ability for the device to remain functional during prolonged exposure to moisture, sweat, water, etc. Failure of the fastener could result in dislodgement of the pad and an unhygienic result. Ultimately, the opposing attachment straps beginning high above the posterior portion of the anal fold, must then complete attachment within the anterior genital region, making it exceedingly difficult for attachment. The question of comfort for males and females alike with this arrangement is entirely dubious.

The rectal absorption pad in U.S. Pat. No. 6,461,341 to J. H. Bennett, a towelette structure, falls short insofar as having a lack of substance, ergonomics and structure. The claimed benefit to such a structure is that minimal sensation within the region is preferable. Based upon these assertions, it must be called into question whether the thinness of a tissue like device is of adequate substance to absorb a potentially heavy release. Also, the touted dual function of an anal and vaginal urine collection device greatly limits the scope of this pad to an essentially female sector. Furthermore, the device assumes that a dual-purpose function is necessary to begin with. Lastly, the flaccid nature of a towel structure, calls into question the hygienic removal of this pad. Although having an extraction tab, it is entirely possible for the folded towel to unfurl during removal greatly increasing the possibility for undesirable fecal/body contact.

The anal patch for fecal incontinence in U.S. Pat. No. 5,695,484 to B. J. Cox proposes a flat circular patch folded into a concave saddle like orientation. Although the curvature ergonomically accommodates the anal cleft, it fails to engage intimately with the anal region, the feature most necessary to adequately ensure maximal protection. Though a proposed embodiment features a more intimate nipple structure, it is rather anemic and unsubstantial calling into question its functional value. Furthermore, this particular embodiment purports to have an invasive ability, which in terms of comfort must be greatly questioned, especially by those who would prefer more intimate contact but wish to avoid potential invasion to the anal opening. Lastly, insertion and retention of the anal patch, is accomplished by an adhesive vehicle applied to the patch. Those with frequent or chronic incontinence symptoms could most certainly experience a considerable degree of dermal irritation associated with chronic exposure and removal of an adhesive based device in this most sensitive region of the body.

BACKGROUND OF INVENTION—OBJECTS AND ADVANTAGES

Accordingly, several objects and advantages of the present patent application of Dominic A. Viscomi and Brian D. Viscomi for "Positive-Pressure Rectal Incontinence Pad" invention are:

(a) Unlike prior art, the rectal pressure pad's superior fit ensures the most intimate and secure barrier possible in the event of accidental discharge.

(b) This rectal pressure pad's unique construction actively helps user to fend bowel urges through counter pressure, greatly improving one's quality of life.

(c) Consistent use over time can allow for the user to bowel train, and attain a degree of mastery over the urgency associated with bowel incontinence.

(d) Anatomically conscious design allows for adhesive-free, non-irritating use, with minimal chance for slippage during active and restful scenarios. One-piece construction maintains integrity during exposure to extreme moisture and during periods prolonged usage.

(e) Presents integrated user-friendly system for precise self-hygienic insertion and removal.

(f) Perforated seam allows for user to control size and contour of rectal pad based upon their desire for comfort.

(g) Serves as a superior vehicle for the application of topical medications and salves.

(h) Can eliminate need for bulky diaper accessory.

(i) May help to lessen the need for medications used to reduce bowel motility.

(j) Aids in bowel retraining for post-colon surgical and pelvic radiation patients.

(k) Enables user to help overcome peristaltic waves until bowel assumes a quiescent state.

(l) Allows for release of gaseous discharge and intestinal pressure build up relief while simultaneously minimizing fecal discharge.

(m) Serves as a collection receptacle for nominal fecal seepage.

(n) Affords both a physiologic and psychological advantage (o) Mucous, or watery seepage is absorbed to maintain dryness and comfort level.

(p) The objects and advantages of our positive pressure rectal pad will become apparent from a consideration of the ensuing illustrations and accompanying descriptions.

SUMMARY

In accordance with the present invention, a rectal pad comprising an absorbent hydrophilic snail shaped body having a compressible node, blade like tail, lateral wings, insertion aperture, and removal tab.

DRAWINGS-Reference Numerals

| 2 | node | 4 | tail |
|---|---|---|---|
| 6 | wings | 8 | anterior stop |
| 10 | insertion aperture | 12 | posterior groove |
| 14 | removal tab | 16 | sheath |
| 18 | perforation seam | 20 | gluteus maximus |
| 22 | anal sphincter | 24 | fecal matter |

DETAILED DESCRIPTION—FIGS. 1A to 5B—PREFERRED EMBODIMENT

Figure 1A:
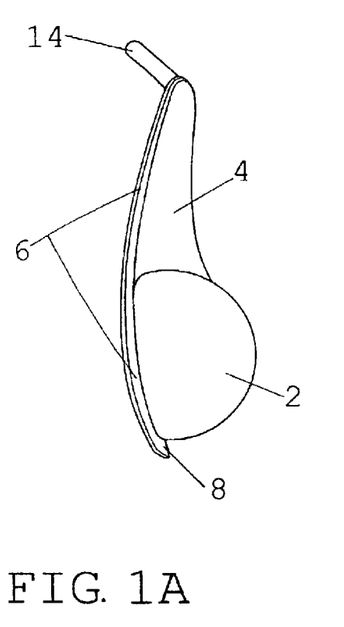
FIGS. 1A to 1D show the side, three quarter, front and back views of the rectal pad.
Figure 1B:
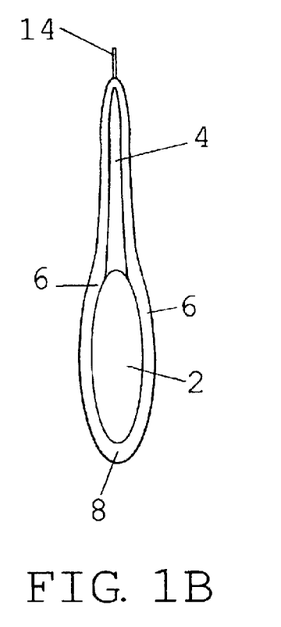
Figure 1C:
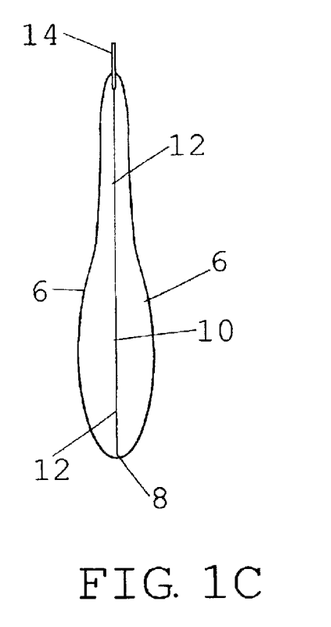
Figure 1D:
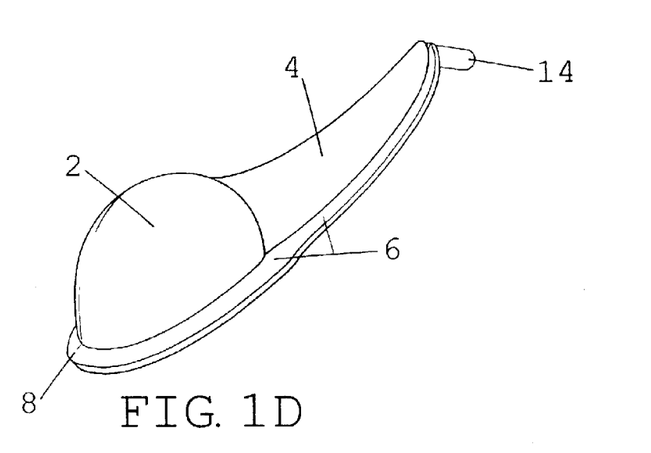

A preferred embodiment of the positive pressure rectal pad is shown in FIG. 1A (Side View) FIG. 1B (Front) 1C (Rear) 1D (Dimensional). The pad has a generally snail shaped body with a pronounced, highly compressible memory protrusion, nodule, or node 2. The node's shape is adaptable to accurately conform to the immediate anal cleft. Adjoining the node is a thin spine or tail 4 structure gently curved and contoured to ergonomically rest between the superior portion of the anal cleft, specifically, between the most powerful contractile areas of the of the gluteus maximus 20 muscle bellies. Adjoining the node 2 and tail 4, are two laterally flaring flaps, strips, or wings 6. Flexible properties of the wings 6 serve to flare out against the interior walls of the gluteus maximus 20. At the forward termination of the wings 6, just below the node 2, a protrusion or a blunted lip serves as an anterior stop 8 to engage the anterior inferior anal rim so as not to impinge upon the genital region. This is valid for both sexes. Located on the inferior aspect of the rectal pad FIG. 1C, a channel or posterior groove 12 runs longitudinally and allows for an opening, or insertion aperture 10 directly under the node for finger placement. Once the fingertip is inserted, the base of the remaining finger shaft rests within the posterior groove 12 allowing the pad to be firmly applied. Located at the top of the tail on the posterior inferior side, a removal ribbon or tab 14 structure protrudes at an angle allowing it to be easily accessed during removal and disposal.

Figure 2A:
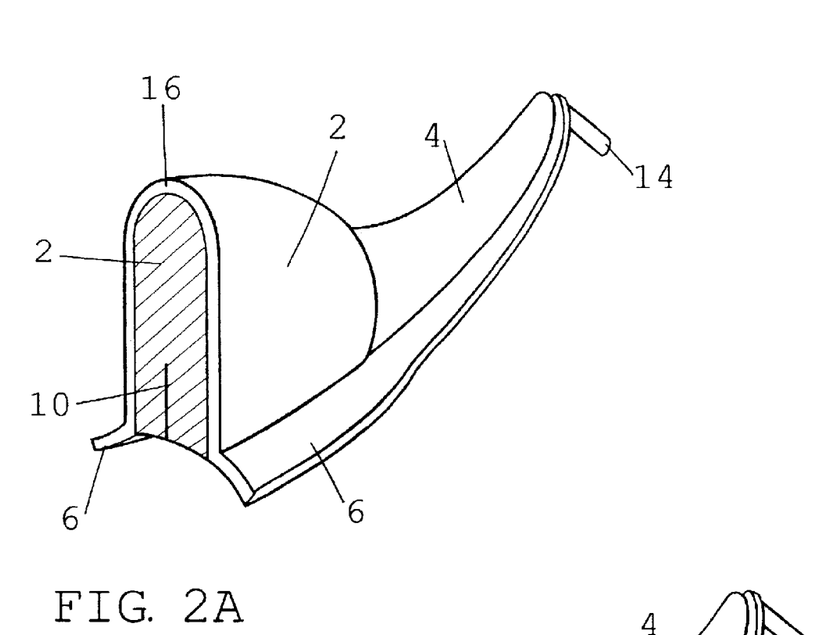
FIGS. 2A to 2B show the effects of pressure being subjected upon the positive-pressure node.
Figure 2B:
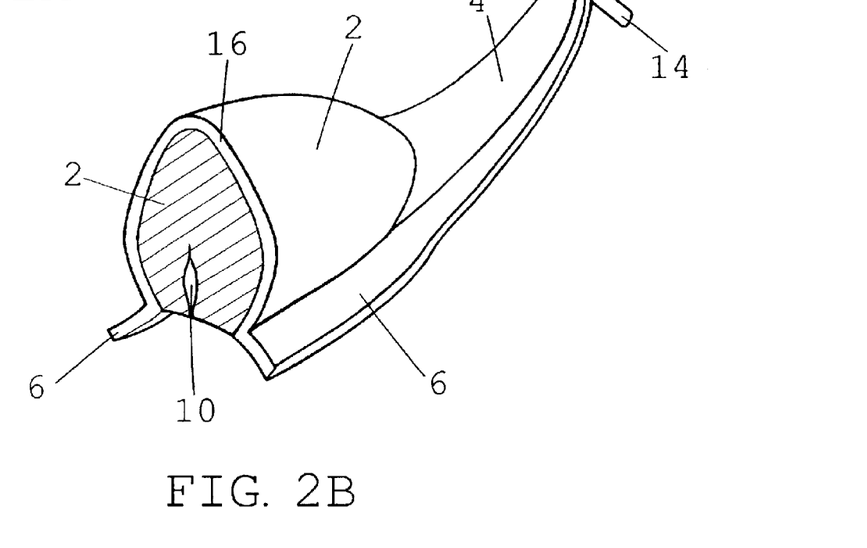

A view of the positive pressure rectal pad shows a cross section of the node FIG. 2A–B. In 2A, a cross section of the preferred embodiment shows the absorbent sheath 16, encased node 2 in a state of full expansion and the wings 6. The vertical line of the insertion aperture appears in the lower central portion of the node 2. In FIG. 2B, externally applied pressure (not shown) illustrates the compressible property of the positive pressure pad's elastic node 2.

Figures 3A, 3B, 3C:
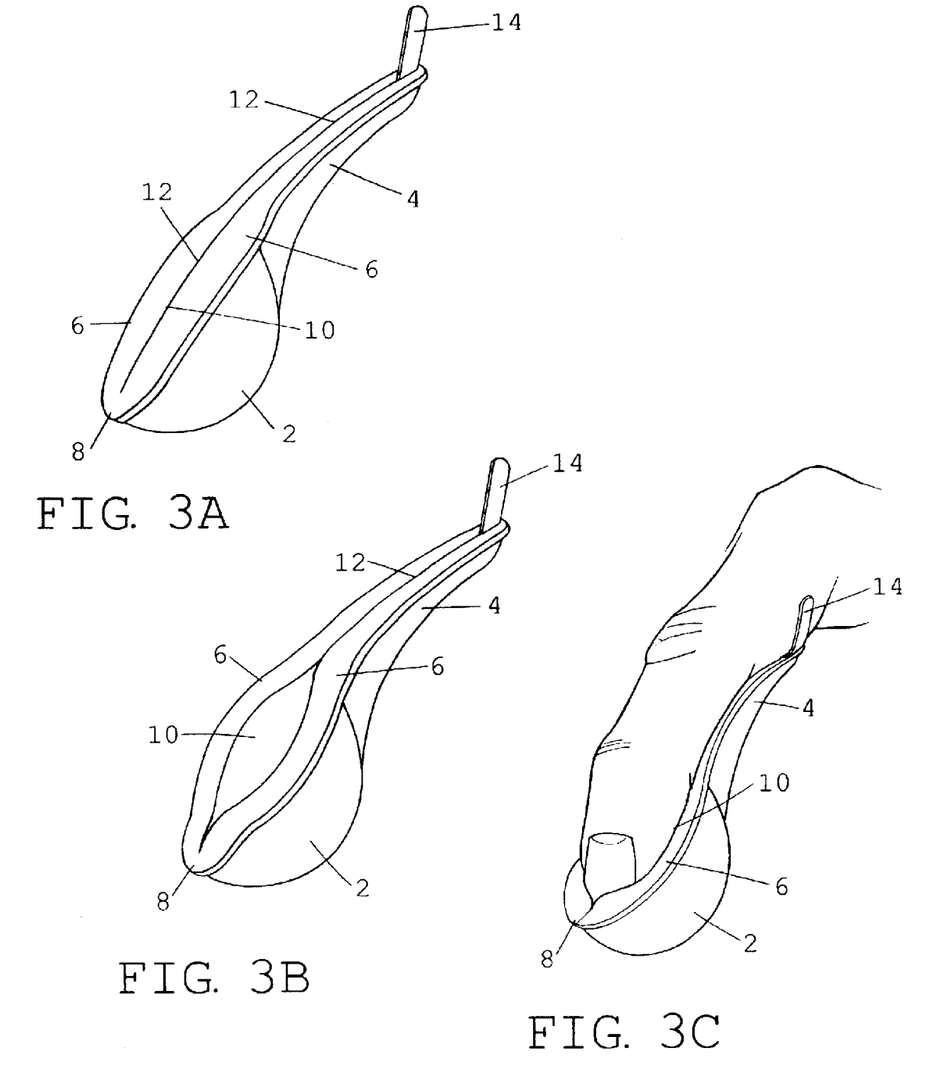
FIGS. 3A to 3C show the posterior finger aperture in closed, open and digital interaction.
Figure 4:
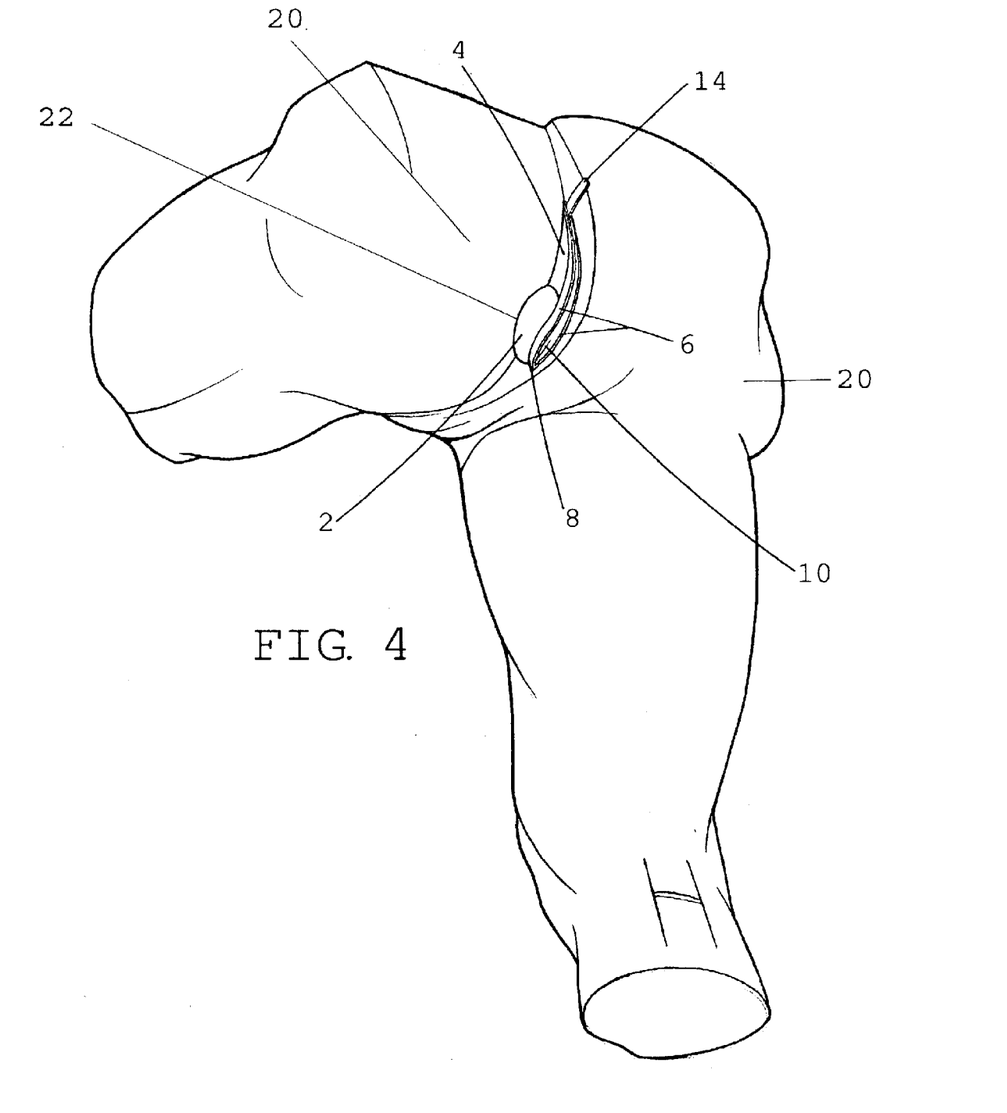
FIG. 4 shows dimensional view of the rectal pad in situ

FIGS. 3A–3C portray the function of the rectal pad's insertion aperture 10. In 3A the insertion aperture 10 is in a neutral or closed position. 3B exhibits the opening of the insertion aperture 10, which allows for the digital insertion of the fingertip into the node 2. FIG. 3C presents the application of the fingertip into the insertion aperture 10 and placement of the finger within the channel of the posterior groove 12. FIG. 4 is a perspective view of the positive pressure rectal pad as it rests within the cleft of the gluteus maximus 20. This figure illustrates the intimacy with which the node 2 and tail 4 conform to the complex curvatures of the anal cleft's anatomy. Intimate anal sphincter 22 contact, is also depicted.

Figure 5A:
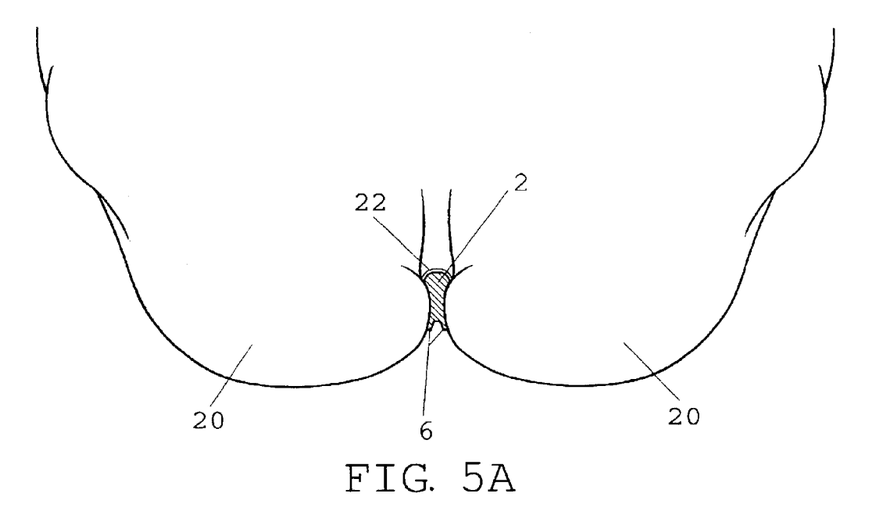
FIGS. 5A to 5B show top down cross-section, illustrating pad with passive positive pressure under active compression during voluntary gluteal contraction.
Figure 5B:
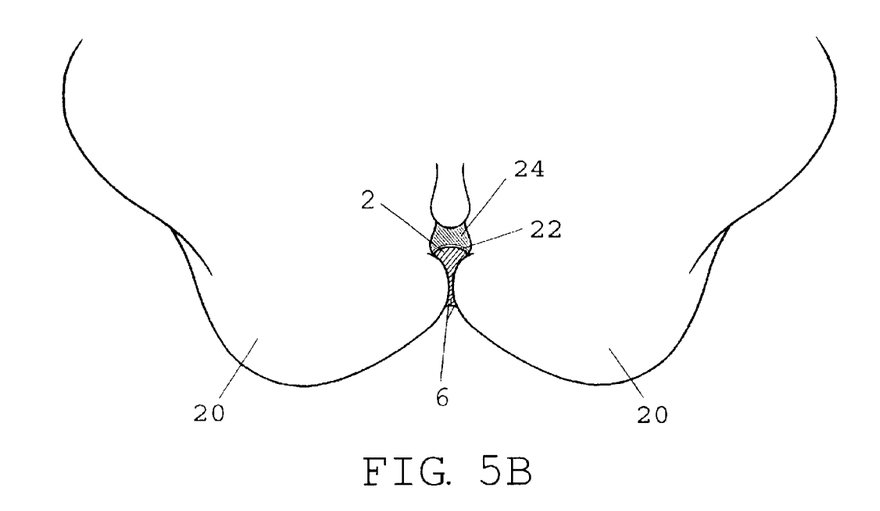

FIGS. 5A to 5B is a top down cross-section overview of the gluteus maximus 20 in relation to the positive pressure rectal pad. 5A exhibits the node 2 in a passive positive pressure state, encountered under normal function. The gluteus maximus 20 is viewed in a relaxed status. FIG. 5B portrays the buttocks in a contractile state demonstrating the node 2 in active positive compression, serving to buttress the anal sphincter 22 to counter against the downward intestinal forces of gas and fecal matter 24.

Our positive pressure rectal pad is preferably molded from an absorbent hydrophilic polymeric material, that is biocompatible and should be sheathed in an outer absorbent layer, composed of a biodegradable cellulose, polyactic acid or cotton fiber. An absorbent, polyurethane foam can also be used which has been rendered biodegradable by the hydrolysis of a weak backbone link, such as an amine group. Other foam materials such as polyofelins can be used and made hydrolytically biodegradable by using weak links such as starches in the polymer backbones. Also a similarly formed foam node structure can be constructed sheathed in an absorbent cellulose, polyactic acid or cotton fiber to create and complete the body of the rectal pad. In addition the entire pad and node structure itself can be a stamped or formed and be comprised of an absorbent cellulose, polyactic acid or cotton fiber.

FIGS. 6A to 10B—ALTERNATIVE EMBODIMENTS

Figure 6A:
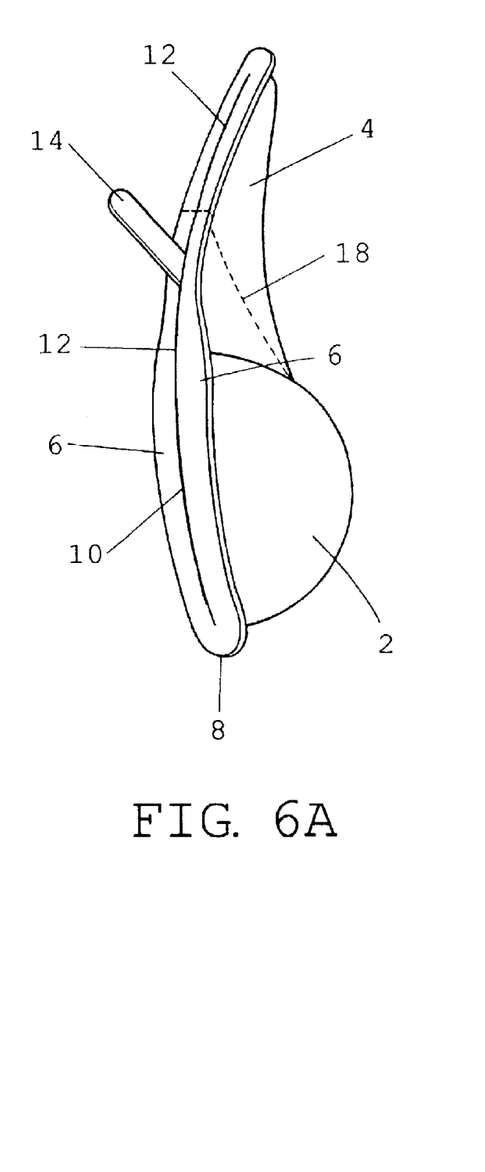
FIGS. 6A to 6B show a rectal pad with a repositioned removal tab and a perforated tail for size adjustment.

FIG. 6A shows an alternative embodiment having a perforated seam 18 to allow tail size adjustment.

Figure 6B:
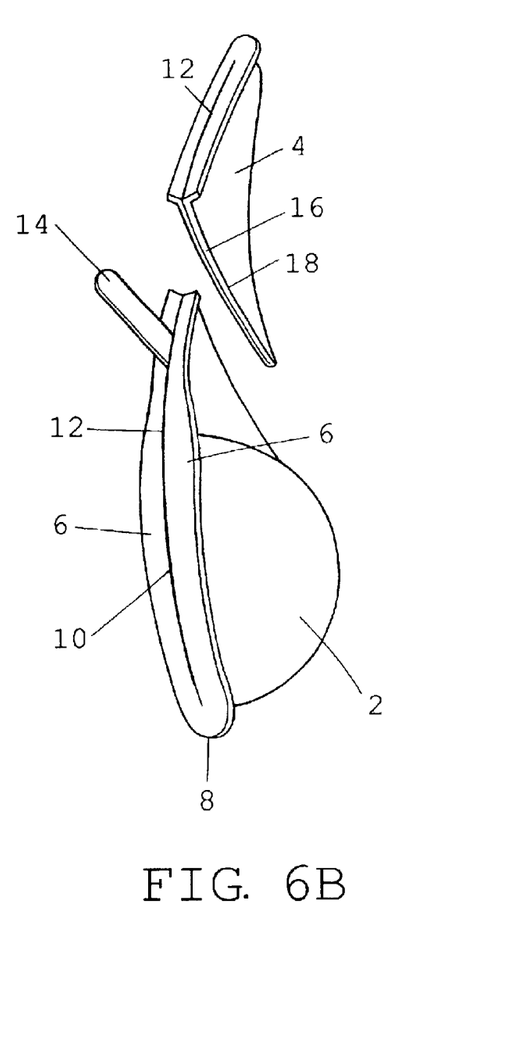

FIG. 6B shows the separation of the upper tail 4 portion of the rectal pad from the lower potion of the tail 4 by tearing along the perforation seam 18

Figure 7:
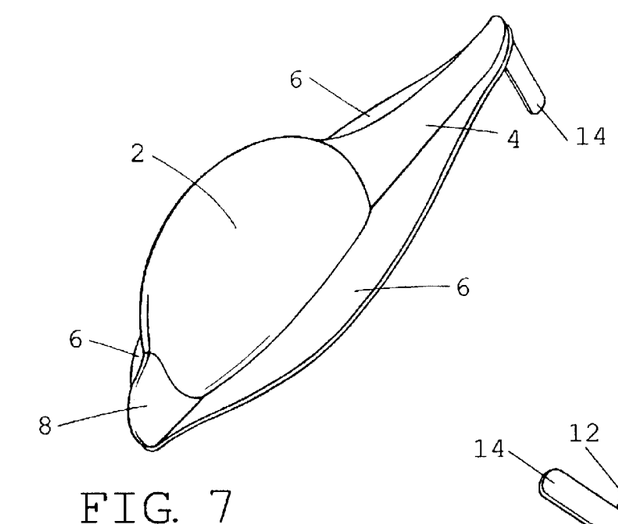
FIG. 7 shows a node with less convexity and a more pronounced anterior stop

FIG. 7 shows the rectal pad with a less convex construction and a more pronounced anterior stop.

Figure 8A:
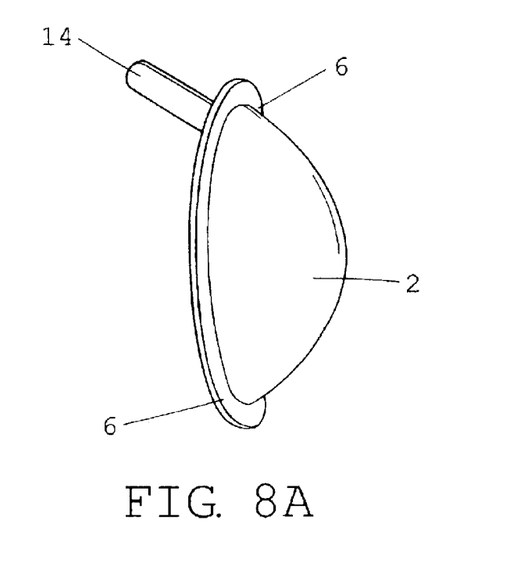
FIGS. 8A to 8B show a three-quarter front and back view of a node centric pad minus a tail.
Figure 8B:
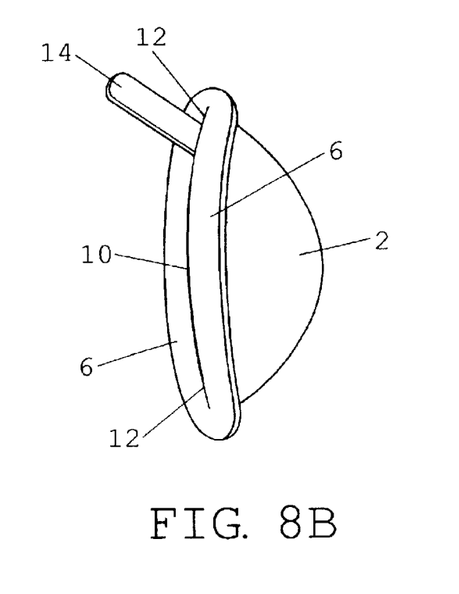

FIG. 8A (Front three quarter) and 8B (Rear three quarter) shows a node 2 centric positive pressure rectal pad design with the tail 4 features eliminated. Emphasis of this design is intended for minimal activity or nighttime non-active use and for those users who prefer a less substantial pad.

Figure 9A:
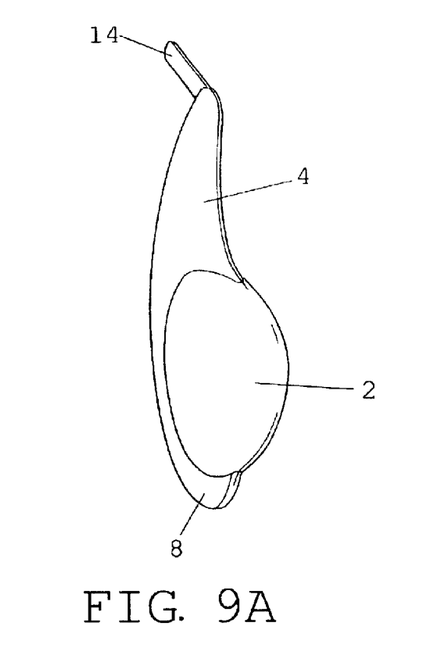
FIGS. 9A to 9B show a three-quarter front and back view of a positive pressure rectal pad with no wings.
Figure 9B:
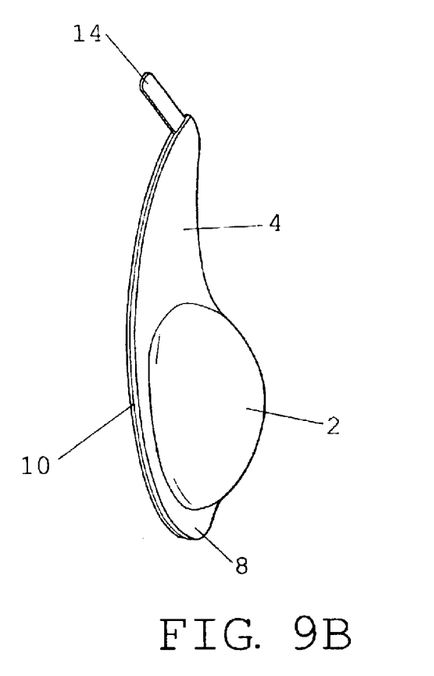

FIG. 9A (Front three quarter) and 9B (Back three quarter) shows the rectal pad with the wing 6 structures removed. Emphasis is placed upon a more streamlined design to effect diminished wearer sensation.

Figure 10A:
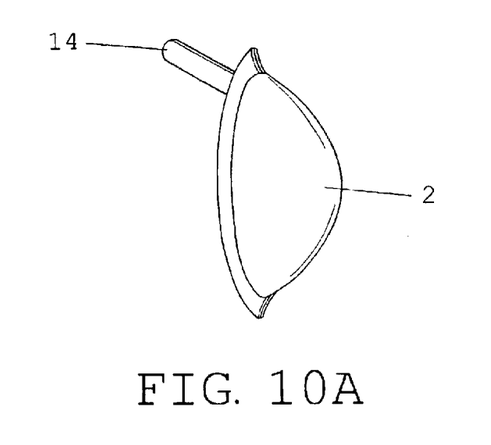
FIGS. 10A to 10B show a three-quarter front and back view of a node centric pad minus both tail and wings.
Figure 10B:
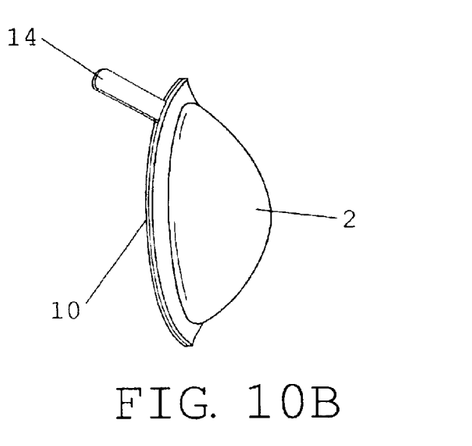

FIG. 10A (Front three quarter) and 10B (Rear three quarter) shows a node 2 centric version of the positive pressure rectal pad with the tail 4 and wing 6 features removed. Emphasis is placed upon a more streamlined design for a more a reduced wearer sensation.

Operation—FIGS. 1,2,3,4,5

To employ the positive pressure rectal pad for active protection and urgency control, one simply inserts the index or other preferred fingertip into the insertion aperture 10 and places the remaining shaft of the finger within the posterior groove 12. Using appropriate fingers, the user directs the wings 6 around the inserted fingertip and finger phalange into the protective groove. From here, the user would proceed to separate the folds of the gluteus maximus 20 and direct the node 2 portion of the positive pressure rectal pad toward the anal sphincter 22. Upon nodal anal contact, additional pressure is applied via the inserted finger to compress the node to the desired comfort level. Proceeding node compression, the user will then secure the inferior portion of the rectal pad by guiding and securing the anterior stop's 8 lip below the anal opening. To complete insertion, the user retains desired degree of node compression and then promptly directs the tail portion of the device into the upper inner region of the buttocks making sure the concave curvature of the tail 4 is contiguous with the inner sacral contour. In the final step of insertion, the wearer of the rectal pad squeezes the gluteus maximus 20 and removes the index finger from the insertion aperture.

With the pad in situ, FIG. 4, the wearer avails of the positive pressure aspects of the node 2 due to its compressibility during insertion. Upon urgency or duress, the wearer contracts the gluteus maximus muscle 20 bellies seen in FIG. 5. Contraction creates a driving inward force to actively compress the node and magnify the pressure of the pad against the anal sphincter 22. This increased pressure, determined by the level of muscle contraction, produces a counter force against the anal sphincter, which aids in resisting the downward pushing of fecal matter 24. When necessary for replacement, the user simply reaches rearward to grasp the removal tab 14 and dislodges the pad from the cleft. Prompt disposal in an appropriate depository completes the cycle of use.

Conclusion, Ramifications, and Scope

Accordingly, the reader will see that the positive pressure function of this pad promotes the highest degree of protection possible through its form fitting form-fitting properties. Superseding the active barrier to potential soiling is the pad's ability to assist the wearer to stave off premature bowel evacuation urges, by contraction of the buttock's 20 musculature. This can be repeated until the bowel returns to a state of tonic normalcy. Additionally, through continued use of the pressure pad, the wearer can help to retrain the regional muscles of the anus and help to gain greater control over urgency, and achieve psychological well being. Furthermore, the constant push of the pad produces stable pressure to help counter less acute symptoms of urgency and to foster security and confidence for the user. Furthermore, the positive pressure rectal pad Permits a user friendly and personally hygienic method of insertion.

Presents a sturdy one-piece design that maintains integrity for hassle free disposal.

Remotely placed tab system allows a user to dispose of pad with minimal risk of exposure to fecal material.

Although the description above contains many specifications, these should not be construed as limiting the scope of the invention but as merely providing illustrations of some of the presently preferred embodiments of this invention. For example, the rectal pad can have other shapes such as ovoid, triangular trapezoidal etc. And have varying anatomical considerations with respect to pad morphology. The node structure can be of a different size and thickness with regard to comfort and or functional properties. In addition, the node's composition can be altered indefinitely with regard to optimal performance and result. Regarding other features, the tail and wings can be tailored to any size or shape that best ensures a stable secure fit with maximal absorption potential. This includes the removal of such structures if necessary. Additional considerations involve rectal pads pre-impregnated with various topical medications and or moisturizing lotions. With regards to odor, the positive pressure rectal pad can be scented with any number of available biocompatible fragrances.

Thus, the scope of the invention should be determined by the appended claims and their legal equivalents, rather than by the example given.

We claim:

1. A rectal pad for use upon the exterior anal opening comprising:

(a) An anatomically sensitive body;

(b) An urging means for producing pressure contiguous to the body;

(c) An absorbent exterior;

wherein said body is a generally snail shaped pad designed to fit within the anal cleft;

wherein said snail shaped pad has a highly compressible nodal structure comprised of an elastic material.

2. The rectal pad of claim 1, wherein said urging means is of an absorbent, elastic, material.

3. The rectal pad of claim 2, wherein said elastic material is foam.

4. The rectal pad of claim 1, wherein said body is a generally snail shaped pad with an ergonomic, anatomical curvature.

5. The rectal pad of claim 1, wherein said snail shaped pad has a thin, gently curved, concave tail, that is contiguous to said nodal structure.

6. The rectal pad of claim 1, wherein said absorbent exterior sheathes said snail shaped body.

7. The rectal pad of claim 1, wherein said absorbent exterior is cotton.

8. A rectal pad for use upon the exterior anal opening comprising:

(a) An anatomically sensitive body;

(b) An urging means for producing pressure contiguous to the body;

(c) An absorbent exterior;

wherein said body is a generally snail shaped pad designed to fit within the anal cleft;

wherein said snail shaped pad has a pair of laterally oriented wings flanking said nodal structure and a tail.

9. The rectal pad of claim 8, wherein said wings create a medial channel called a posterior groove on the rearward potion of said snail shaped pad.

10. The rectal pad of claim 9, wherein a finger tip sized aperture arises between said posterior groove and inserts a short distance into said nodal structure.

11. The rectal pad of claim 8, wherein a removal tab emerges from a posterior groove.

12. The rectal pad of claim 8, wherein said urging means is of an absorbent, elastic, material.

13. The rectal pad of claim 12, wherein said elastic material is foam.

14. The rectal pad of claim 8, wherein said body is a generally snail shaped pad with an ergonomic, anatomical curvature.

15. The rectal pad of claim 8, wherein said snail shaped pad has a thin, gently curved, concave tail, that is contiguous to said nodal structure.

16. The rectal pad of claim 8, wherein said absorbent exterior sheathes said snail shaped body.

17. The rectal pad of claim 8, wherein said absorbent exterior is cotton.

* * * * *